United States Patent
Hopkins et al.

(10) Patent No.: US 6,530,939 B1
(45) Date of Patent: Mar. 11, 2003

(54) VASCULAR DEVICE HAVING ARTICULATION REGION AND METHODS OF USE

(75) Inventors: Leo N. Hopkins, Buffalo, NY (US); Farhad Khosravi, San Mateo, CA (US); Amr Salahieh; Jeff A. Krolik, both of Campbell, CA (US); Jackson F. Demond, Santa Cruz, CA (US)

(73) Assignee: Incept, LLC, San Mateo, CA (US)

( * ) Notice: Subject to any disclaimer, the term of this patent is extended or adjusted under 35 U.S.C. 154(b) by 0 days.

(21) Appl. No.: 09/364,064

(22) Filed: Jul. 30, 1999

(51) Int. Cl.$^7$ .............................................. A61M 29/00
(52) U.S. Cl. ........................ 606/200; 606/194; 606/198
(58) Field of Search ................................ 606/200, 194, 606/198; 604/22, 96.01, 104

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | |
| 3,683,904 A | 8/1972 | Forster | |
| 3,889,657 A | 6/1975 | Baumgarten | 128/2 |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/12 |

(List continued on next page.)

FOREIGN PATENT DOCUMENTS

| | | | |
|---|---|---|---|
| DE | 28 21 048 | 7/1980 | ............ A61B/17/22 |
| DE | 34 17 738 | 11/1985 | ............ A61M/1/34 |
| DE | 40 30 998 A1 | 10/1990 | ............ A61F/2/01 |
| DE | 199 16 162 | 10/2000 | |
| EP | 0 200 688 | 11/1986 | ............ A61B/17/22 |
| EP | 0 293 605 A1 | 12/1988 | ............. A61F/2/02 |
| EP | 0 411 118 A1 | 2/1991 | ............ A61M/25/00 |
| EP | 0 427 429 A2 | 5/1991 | .......... A61M/25/10 |
| EP | 0 427 429 A1 | 5/1991 | .......... A61M/25/10 |
| EP | 0 437 121 B1 | 7/1991 | ............. A61F/2/02 |
| EP | 0 472 368 A2 | 2/1992 | ............ A61B/17/22 |
| EP | 0 533 511 A1 | 3/1993 | .......... A61M/29/02 |

(List continued on next page.)

OTHER PUBLICATIONS

Wholey, Mark H. et al., "PTA and Stents in the Treatment of Extracranial Circulation," *The Journal of Invasive Cardiology: vol. 8/Supplement E,* Health Management Publications, Inc., 1996, pp. 25E–30E.

(List continued on next page.)

*Primary Examiner*—Gary Jackson
(74) *Attorney, Agent, or Firm*—Crompton, Seager & Tufte LLC

(57) ABSTRACT

Apparatus and methods are provided for use in filtering emboli from a vessel and performing thrombectomy and embolectomy, wherein a vascular device comprises a support hoop having an articulation region connected near a distal end of a guide wire, and a blood permeable sac affixed to the support hoop so that the support hoop forms a mouth of the blood permeable sac. The articulation region comprises a reduced thickness region of the support hoop that prevents kinks from forming in the support hoop when the apparatus is contracted to its delivery state, and curved regions that close the mouth of the sac to prevent material escaping from the sac when the apparatus is collapsed for removal.

43 Claims, 5 Drawing Sheets

U.S. PATENT DOCUMENTS

| | | |
|---|---|---|
| 4,705,517 A | 11/1987 | DiPisa, Jr. .................... 623/12 |
| 4,706,671 A | 11/1987 | Weinrib ...................... 128/348 |
| 4,723,549 A | 2/1988 | Wholey et al. |
| 4,728,319 A | 3/1988 | Masch ......................... 604/22 |
| 4,733,665 A | 3/1988 | Palmaz ...................... 128/343 |
| 4,790,812 A | 12/1988 | Hawkins, Jr. et al. ........ 604/22 |
| 4,790,813 A | 12/1988 | Kensey ........................ 604/22 |
| 4,794,928 A | 1/1989 | Kletschka .................. 128/344 |
| 4,794,931 A | 1/1989 | Yock ..................... 128/660.03 |
| 4,800,882 A | 1/1989 | Gianturco .................. 128/343 |
| 4,807,626 A | 2/1989 | McGirr ...................... 128/328 |
| 4,842,579 A | 6/1989 | Shiber ......................... 606/22 |
| 4,857,045 A | 8/1989 | Rydell ......................... 604/22 |
| 4,857,046 A | 8/1989 | Stevens et al. ............... 604/22 |
| 4,867,157 A | 9/1989 | McGurk-Burleson et al. ........... 128/305 |
| 4,873,978 A | 10/1989 | Ginsburg .................... 128/345 |
| 4,898,575 A | 2/1990 | Fischell et al. ............... 604/22 |
| 4,907,336 A | 3/1990 | Gianturco .................... 29/515 |
| 4,921,478 A | 5/1990 | Solano et al. ................. 604/53 |
| 4,921,484 A | 5/1990 | Hillstead .................... 604/104 |
| 4,926,858 A | 5/1990 | Gifford et al. ............... 606/159 |
| 4,950,277 A | 8/1990 | Farr ........................... 606/159 |
| 4,955,895 A | 9/1990 | Sugiyama et al. .......... 606/194 |
| 4,957,482 A | 9/1990 | Shiber ......................... 604/22 |
| 4,969,891 A | 11/1990 | Gewertz ..................... 606/200 |
| 4,979,951 A | 12/1990 | Simpson ..................... 606/159 |
| 4,986,807 A | 1/1991 | Farr ............................. 604/22 |
| 4,998,539 A | 3/1991 | Delsanti ..................... 128/898 |
| 5,002,560 A | 3/1991 | Machold et al. ............. 606/198 |
| RE33,569 E | 4/1991 | Gifford, III et al. ........ 606/159 |
| 5,007,896 A | 4/1991 | Shiber ......................... 604/22 |
| 5,007,917 A | 4/1991 | Evans ........................ 606/170 |
| 5,011,488 A | 4/1991 | Ginsburg .................... 606/159 |
| 5,019,088 A | 5/1991 | Farr ........................... 606/159 |
| 5,041,126 A | 8/1991 | Gianturco .................... 606/195 |
| 5,053,008 A | 10/1991 | Bajaj ........................... 604/104 |
| 5,053,044 A | 10/1991 | Mueller et al. .............. 606/159 |
| 5,071,407 A | 12/1991 | Termin et al. ............... 604/104 |
| 5,071,425 A | 12/1991 | Gifford, III et al. ........ 606/159 |
| 5,085,662 A | 2/1992 | Willard ...................... 606/159 |
| 5,087,265 A | 2/1992 | Summers .................... 606/159 |
| 5,100,423 A | 3/1992 | Fearnot ........................ 606/15 |
| 5,100,424 A | 3/1992 | Jang et al. ................... 606/159 |
| 5,100,425 A | 3/1992 | Fischell et al. ............. 606/159 |
| 5,102,415 A | 4/1992 | Guenther et al. ........... 606/159 |
| 5,104,399 A | 4/1992 | Lazarus ......................... 623/1 |
| 5,108,419 A | 4/1992 | Reger et al. ................. 606/200 |
| 5,133,733 A | 7/1992 | Rasmussen et al. ........ 606/200 |
| 5,135,531 A | 8/1992 | Shiber ........................ 606/159 |
| 5,152,771 A | 10/1992 | Sabbaghian et al. ........ 606/159 |
| 5,152,777 A | 10/1992 | Goldberg et al. ........... 606/200 |
| 5,160,342 A | 11/1992 | Reger et al. ................. 606/200 |
| 5,171,233 A | 12/1992 | Amplatz et al. ............. 604/281 |
| 5,190,546 A | 3/1993 | Jervis ........................... 606/78 |
| 5,195,955 A | 3/1993 | Don Michael ............... 604/22 |
| 5,224,953 A | 7/1993 | Morgentaler ................ 606/192 |
| 5,306,286 A | 4/1994 | Stack et al. .................. 606/198 |
| 5,314,444 A | 5/1994 | Gianturco .................... 606/195 |
| 5,314,472 A | 5/1994 | Fontaine ....................... 623/12 |
| 5,318,576 A | 6/1994 | Plassche, Jr. et al. ....... 606/159 |
| 5,329,942 A | 7/1994 | Gunther et al. .............. 128/898 |
| 5,330,484 A | 7/1994 | Gunther ....................... 606/128 |
| 5,330,500 A | 7/1994 | Song ............................ 606/198 |
| 5,350,398 A | 9/1994 | Pavcnik et al. .............. 606/200 |
| 5,354,310 A | 10/1994 | Garnic et al. ................ 606/198 |
| 5,356,423 A | 10/1994 | Tihon et al. .................. 606/194 |
| 5,366,464 A | 11/1994 | Belknap ....................... 606/159 |
| 5,366,473 A | 11/1994 | Winston et al. .............. 606/198 |
| 5,370,657 A | 12/1994 | Irie ............................. 606/200 |
| 5,370,683 A | 12/1994 | Fontaine ......................... 623/1 |
| 5,376,100 A | 12/1994 | Lefebvre ..................... 606/180 |
| 5,383,887 A | 1/1995 | Nadal ......................... 606/200 |
| 5,383,892 A | 1/1995 | Cardon et al. .............. 606/198 |
| 5,383,926 A | 1/1995 | Lock et al. ..................... 623/1 |
| 5,387,235 A | 2/1995 | Chuter ........................... 623/1 |
| 5,395,349 A | 3/1995 | Quiachon et al. ........... 604/248 |
| 5,397,345 A | 3/1995 | Lazerus ......................... 623/1 |
| 5,405,377 A | 4/1995 | Cragg ............................. 623/1 |
| 5,409,454 A | 4/1995 | Fischell et al. ................ 604/22 |
| 5,415,630 A | 5/1995 | Gory et al. .................... 604/53 |
| 5,419,774 A | 5/1995 | Willard et al. ................ 604/22 |
| 5,421,832 A | 6/1995 | Lefebvre ....................... 604/53 |
| 5,423,742 A | 6/1995 | Theron ......................... 604/28 |
| 5,423,885 A | 6/1995 | Williams ........................ 623/1 |
| 5,425,765 A | 6/1995 | Tiefenbrun et al. ........... 623/12 |
| 5,443,498 A | 8/1995 | Fontaine ......................... 623/1 |
| 5,449,372 A | 9/1995 | Schmaltz et al. ........... 606/198 |
| 5,456,667 A | 10/1995 | Ham et al. ................... 604/107 |
| 5,462,529 A | 10/1995 | Simpson et al. ............. 604/101 |
| 5,476,104 A | 12/1995 | Sheahon ...................... 128/757 |
| 5,484,418 A | 1/1996 | Quiachon et al. ........... 604/167 |
| 5,507,767 A | 4/1996 | Maeda et al. ................ 606/198 |
| 5,512,044 A | 4/1996 | Duer ............................. 604/22 |
| 5,527,354 A | 6/1996 | Fontaine et al. ................ 623/1 |
| 5,536,242 A | 7/1996 | Willard et al. ................ 604/30 |
| 5,540,707 A | 7/1996 | Ressemann et al. ........ 606/159 |
| 5,549,626 A | 8/1996 | Miller et al. ................. 606/200 |
| 5,562,724 A | 10/1996 | Vowerk et al. .................. 623/1 |
| 5,569,274 A | 10/1996 | Rapacki et al. .............. 606/158 |
| 5,569,275 A | 10/1996 | Kotula et al. ................ 606/159 |
| 5,634,897 A | 6/1997 | Dance et al. .................. 604/35 |
| 5,658,296 A | 8/1997 | Bates et al. .................. 606/127 |
| 5,662,671 A | 9/1997 | Barbut et al. ................ 606/170 |
| 5,669,933 A | 9/1997 | Simon et al. ................ 600/200 |
| 5,695,519 A | 12/1997 | Summers et al. ............ 606/200 |
| 5,709,704 A | 1/1998 | Nott et al. ................... 606/200 |
| 5,720,764 A | 2/1998 | Naderlinger ................. 606/200 |
| 5,728,066 A | 3/1998 | Daneshvar .................... 604/96 |
| 5,746,758 A | 5/1998 | Nordgren et al. ........... 606/159 |
| 5,749,848 A | 5/1998 | Jang et al. ..................... 604/53 |
| 5,769,816 A | 6/1998 | Barbut et al. .................. 604/96 |
| 5,779,716 A | 7/1998 | Cano et al. .................. 606/114 |
| 5,792,157 A | 8/1998 | Mische et al. |
| 5,792,300 A | 8/1998 | Inderbitzen et al. ... 156/244.13 |
| 5,795,322 A | 8/1998 | Boudewijn ................... 604/22 |
| 5,797,952 A | 8/1998 | Klein .......................... 606/198 |
| 5,800,457 A | 9/1998 | Gelbfish ...................... 606/200 |
| 5,800,525 A | 9/1998 | Bachinski et al. .............. 623/1 |
| 5,810,874 A | 9/1998 | Lefebvre ..................... 606/200 |
| 5,814,064 A | 9/1998 | Daniel et al. ................ 606/200 |
| 5,817,102 A | 10/1998 | Johnson et al. .............. 606/108 |
| 5,827,324 A | 10/1998 | Cassell et al. ............... 606/200 |
| 5,833,644 A | 11/1998 | Zadino-Azizi et al. ........ 604/52 |
| 5,833,650 A | 11/1998 | Imran ............................ 604/53 |
| 5,846,260 A | 12/1998 | Maahs ......................... 606/200 |
| 5,848,964 A | 12/1998 | Samuels ...................... 600/200 |
| 5,876,367 A | 3/1999 | Kaganov et al. ............... 604/8 |
| 5,893,867 A | 4/1999 | Bagaoisan et al. .......... 606/198 |
| 5,895,399 A | 4/1999 | Barbut et al. ................ 606/159 |
| 5,902,263 A | 5/1999 | Patterson et al. ............. 604/22 |
| 5,906,618 A | 5/1999 | Larson, III .................. 606/108 |
| 5,908,435 A | 6/1999 | Samuels ...................... 606/200 |
| 5,910,154 A | 6/1999 | Tsugita et al. ............... 606/200 |
| 5,911,734 A | 6/1999 | Tsugita et al. ............... 606/200 |
| 5,916,193 A | 6/1999 | Stevens et al. ................ 604/53 |
| 5,925,016 A | 7/1999 | Chrnenky et al. ............. 604/96 |
| 5,925,060 A | 7/1999 | Forber ......................... 606/191 |
| 5,925,062 A | 7/1999 | Purdy ......................... 606/200 |

| | | | | | | | | |
|---|---|---|---|---|---|---|---|---|
| 5,925,063 | A | 7/1999 | Khosravi | 606/200 | EP | 0 696 447 A2 | 2/1996 | A61F/2/06 |
| 5,928,203 | A | 7/1999 | Davey et al. | 604/247 | EP | 0 737 450 A1 | 10/1996 | A61F/2/01 |
| 5,928,218 | A | 7/1999 | Gelbfish | 604/540 | EP | 0 743 046 A1 | 11/1996 | A61F/2/01 |
| 5,934,284 | A | 8/1999 | Plaia et al. | 128/898 | EP | 0 759 287 A1 | 2/1997 | A61F/2/01 |
| 5,935,139 | A | 8/1999 | Bates | 606/159 | EP | 0 771 549 A2 | 5/1997 | A61F/2/01 |
| 5,938,645 | A | 8/1999 | Gordon | 604/264 | EP | 0 784 988 A1 | 7/1997 | A61M/5/165 |
| 5,941,869 | A | 8/1999 | Patterson et al. | 604/508 | EP | 0 852 132 A1 | 7/1998 | A61F/2/01 |
| 5,941,896 | A | 8/1999 | Kerr | 606/200 | EP | 1 127 556 A2 | 8/2001 | |
| 5,947,995 | A | 9/1999 | Samuels | 606/200 | FR | 2 580 504 | 10/1986 | A61M/1/00 |
| 5,951,585 | A | 9/1999 | Cathcart et al. | 606/198 | FR | 2 643 250 A1 | 8/1990 | A61B/17/00 |
| 5,954,745 | A | 9/1999 | Gertler et al. | 606/200 | FR | 2 666 980 | 3/1992 | A61F/2/02 |
| 5,976,172 | A | 11/1999 | Homsma et al. | 606/200 | FR | 2 694 687 | 8/1992 | |
| 5,980,555 | A | 11/1999 | Barbut et al. | | FR | 2 768 326 A1 | 3/1999 | A61F/02/01 |
| 5,989,210 | A | 11/1999 | Morris et al. | 604/22 | GB | 2 020 557 | 11/1979 | A61B/17/50 |
| 5,989,271 | A | 11/1999 | Bonnette et al. | 606/159 | JP | 8-187294 A | 7/1996 | A61M/29/00 |
| 5,989,281 | A | 11/1999 | Barbut et al. | 606/200 | RU | 764684 | 9/1980 | A61M/25/00 |
| 5,993,469 | A | 11/1999 | McKenzie et al. | 606/159 | WO | WO 92/03097 | 3/1992 | A61B/17/00 |
| 5,997,557 | A | 12/1999 | Barbut et al. | 606/159 | WO | WO 94/14389 | 7/1994 | A61F/2/02 |
| 6,001,118 | A | 12/1999 | Daniel et al. | 606/200 | WO | WO 94/24946 | 11/1994 | A61B/17/22 |
| 6,007,557 | A | 12/1999 | Ambrisco et al. | 606/200 | WO | WO 96/01591 | 1/1996 | A61B/17/22 |
| 6,010,522 | A | 1/2000 | Barbut et al. | 606/200 | WO | WO 96/10375 | 4/1996 | A61F/2/06 |
| 6,013,085 | A | 1/2000 | Howard | 606/108 | WO | WO 96/19941 | 7/1996 | A61B/17/00 |
| 6,027,520 | A | 2/2000 | Tsugita et al. | 606/200 | WO | WO 96/23441 | 8/1996 | A61B/5/00 |
| 6,042,598 | A | 3/2000 | Tsugita et al. | | WO | WO 96/33677 | 10/1996 | A61F/11/00 |
| 6,051,014 | A | 4/2000 | Jang | 606/200 | WO | WO 97/17100 | 5/1997 | A61M/29/00 |
| 6,051,015 | A | 4/2000 | Maahs | 606/200 | WO | WO 97/27808 | 8/1997 | A61B/17/22 |
| 6,053,932 | A | 4/2000 | Daniel et al. | 606/200 | WO | WO 97/42879 | 11/1997 | A61B/17/00 |
| 6,059,814 | A | 5/2000 | Ladd | 606/200 | WO | WO 98/02084 | 1/1998 | |
| 6,066,149 | A | 5/2000 | Samson et al. | 606/200 | WO | WO 98/02112 | 1/1998 | A61F/2/01 |
| 6,068,645 | A | 5/2000 | Tu | 606/200 | WO | WO 98/23322 | 6/1998 | A61M/29/00 |
| 6,086,605 | A | 7/2000 | Barbut et al. | 606/200 | WO | WO 98/33443 | 8/1998 | A61B/17/22 |
| 6,117,154 | A | 9/2000 | Barbut et al. | 606/200 | WO | WO 98/34673 | 8/1998 | A61M/31/00 |
| 6,129,739 | A | 10/2000 | Khosravi | 606/200 | WO | WO 98/36786 | 8/1998 | A61M/5/32 |
| 6,136,016 | A | 10/2000 | Barbut et al. | 606/200 | WO | WO 98/38920 | 9/1998 | A61B/17/22 |
| 6,142,987 | A | 11/2000 | Tsugita | 604/500 | WO | WO 98/38929 | 9/1998 | A61B/17/00 |
| 6,152,946 | A | 11/2000 | Broome et al. | 606/200 | WO | WO 98/39046 | 9/1998 | A61M/25/00 |
| 6,165,200 | A | 12/2000 | Tsugita et al. | 606/200 | WO | WO 98/39053 | 9/1998 | A61M/29/00 |
| 6,168,579 | B1 | 1/2001 | Tsugita | 604/96.01 | WO | WO 98/46297 | 10/1998 | A61M/29/00 |
| 6,171,327 | B1 | 1/2001 | Daniel et al. | 606/200 | WO | WO 98/47447 | 10/1998 | A61F/2/06 |
| 6,171,328 | B1 | 1/2001 | Addis | 606/200 | WO | WO 98/49952 | 11/1998 | A61B/17/32 |
| 6,179,851 | B1 | 1/2001 | Barbut et al. | 606/159 | WO | WO 98/50103 | 11/1998 | A61M/29/00 |
| 6,179,859 | B1 | 1/2001 | Bates et al. | 606/200 | WO | WO 98/51237 | 11/1998 | A61F/2/01 |
| 6,179,861 | B1 | 1/2001 | Khosravi et al. | 606/200 | WO | WO 98/55175 | 12/1998 | A61M/29/00 |
| 6,203,561 | B1 | 3/2001 | Ramee et al. | 606/200 | WO | WO 99/09895 | 3/1999 | A61B/17/12 |
| 6,206,868 | B1 | 3/2001 | Parodi | 606/200 | WO | WO 99/22673 | 5/1999 | A61F/2/01 |
| 6,214,026 | B1 | 4/2001 | Lepak et al. | 606/200 | WO | WO 99/23976 | 5/1999 | A61F/2/01 |
| 6,221,006 | B1 | 4/2001 | Dubrul et al. | 606/200 | WO | WO 99/25252 | 5/1999 | A61B/17/00 |
| 6,224,620 | B1 | 5/2001 | Maahs | 606/200 | WO | WO 99/30766 | 6/1999 | A61M/29/00 |
| 6,231,544 | B1 | 5/2001 | Tsugita et al. | 606/200 | WO | 0 934 729 | 8/1999 | A61B/17/22 |
| 6,235,044 | B1 | 5/2001 | Root et al. | 606/200 | WO | WO 99/40964 | 8/1999 | A61M/29/02 |
| 6,235,045 | B1 | 5/2001 | Barbut et al. | 606/200 | WO | WO 99/72059 | 8/1999 | A61F/2/06 |
| 6,238,412 | B1 | 5/2001 | Dubrul et al. | 606/200 | WO | WO 99/44510 | 9/1999 | A61B/17/00 |
| 6,245,087 | B1 | 6/2001 | Addis | 606/200 | WO | WO 99/44542 | 9/1999 | A61F/2/06 |
| 6,245,088 | B1 | 6/2001 | Lowery | 606/200 | WO | WO 99/55236 | 11/1999 | A61B/17/00 |
| 6,245,089 | B1 | 6/2001 | Daniel et al. | 606/200 | WO | WO 99/58068 | 11/1999 | A61B/17/22 |
| 6,258,115 | B1 | 7/2001 | Dubrul | 606/200 | WO | WO 00/07521 | 2/2000 | |
| 6,264,663 | B1 | 7/2001 | Cano | 606/114 | WO | WO 00/07655 | 2/2000 | A61M/29/00 |
| 6,264,672 | B1 | 7/2001 | Fisher | 606/200 | WO | WO 00/09054 | 2/2000 | A61F/7/12 |
| 6,270,513 | B1 | 8/2001 | Tsugita et al. | 606/203 | WO | WO 00/16705 | 3/2000 | A61B/17/22 |
| 6,277,138 | B1 | 8/2001 | Levinson et al. | 606/200 | WO | WO 00/49970 | 8/2000 | A61F/2/01 |
| 6,277,139 | B1 | 8/2001 | Levinson et al. | 606/200 | WO | WO 00/53120 | 9/2000 | |
| 6,280,413 | B1 | 8/2001 | Clark et al. | 604/704 | WO | WO 00/67664 | 11/2000 | |
| 6,287,321 | B1 | 9/2001 | Jang | 606/200 | WO | WO 00/67665 | 11/2000 | |
| 6,290,710 | B1 | 9/2001 | Cryer et al. | 606/200 | WO | WO 00/67666 | 11/2000 | |
| 6,309,399 | B1 | 10/2001 | Barbut et al. | 606/159 | WO | WO 00/67668 | 11/2000 | |
| 6,319,268 | B1 | 11/2001 | Ambrisco et al. | 606/200 | WO | WO 00/67669 | 11/2000 | |
| 6,344,049 | B1 | 2/2002 | Levinson et al. | 606/200 | WO | WO 01/05462 | 1/2001 | |
| | | | | | WO | WO 01/08595 | 2/2001 | |
| | | FOREIGN PATENT DOCUMENTS | | | WO | WO 01/08596 | 2/2001 | |
| EP | | 0 655 228 A1 | 11/1994 | A61F/2/02 | WO | WO 01/08742 | 2/2001 | |
| EP | | 0 686 379 A2 | 6/1995 | A61F/2/06 | WO | WO 01/08743 | 2/2001 | |

| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

Fadali, A. Moneim, "A filtering device for the prevention of particulate embolization during the course of cardiac surgery", *Surgery*, vol. 64(3), pp. 634–639 (Sep. 1968).

"Atherosclerotic Disease of the Aortic Arch as a Risk Factor Of Recurrent Ischemic Stroke,," *The New England Journal of Medicine*, pp. 1216–1221 (May 1996).

"Endovascular Grafts, Stents Drive Interventional Radiology Growth,"*Cardiovascular Device Update*, 2(3):1–12 (Mar. 1996).

"Protruding Atheromas in the Thoracic Aortic and Systemic Embolization," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601–604.

Cragg, Andrew et al; "Nonsurgical Placement of Arterial Endoprosthesis: A New Technique Using NItinol Wire," *AJR*, pp. 261–263 (Apr. 1983).

Diethrich et al., "Percutaneous Techniques for Endoluminal Carotid Interventions," *J. Endovasc. Surg.*, 3:182–202 (1996).

Haissaguerre et al., "Spontaneous Initiation of Atrial Fibrillation by Ectopic Beats Originating in the Pulmonary Veins," *The New England Journal of Medicine*, 339(10):659–666 (Sep. 1988).

Jordan, Jr. et al., "Microemboli Detected by Transcranial Doppler Monitoring...," *Cardiovascular Surgery*, 7(1033–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," *Laboratory Investigation*, 69(4):772–774 (Apr. 1984).

Marache et al., "Percutaneous Transluminal Venous Angioplasty...," *American Heart Journal*, 125(2 Pt 1):362–366 (Feb. 1993).

Mazur et al., "Directional Atherectomy with the Omnicath™: A Unique New Catheter System," Catheterization and Cardiovascular Diagnosis, 31:17–84 (1994).

Moussa, MD, Issam "Stents Don't Require Systemic Anticoagulation... But the Technique (and Results) Must be Optimal," *Journal of Invasive Cardiol.*, 8(E):3E–7E, (1996).

Nakanishi et al., "Catheter Intervention to Venous System Using Expandable Metallic Stents," *Rinsho Kyobu Geka*14(2): English Abstract Only (Apr. 1994).

Onal et al., "Primary Stenting for Complex Atherosclerotic Plaques in Aortic and Iliac Stenoses," *Cardiovascular & Interventional Radiology*, 21(5):386–392 (1998).

Theron et al., "New Triple Coaxial Catheter System for Carotid Angioplasty with Cerebral Protection," *American Journal of Neuroradiology*, 11:869–874 (1990).

Tunick et al., "Protruding atheroslerotic plaque in the aortic archo f patients with systemic embolization: A new finding seen by transesophageal echocardiography," *American Heart Journal*, 120(3):658–660 (Sep. 1990).

Waksman et al., "Distal Embolization is Common After Directional Atherectomy...," *American Heart Journal*, 129(3):430–435 (1995).

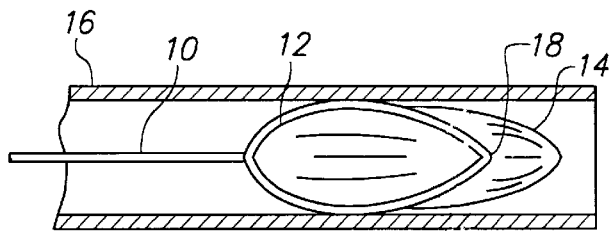
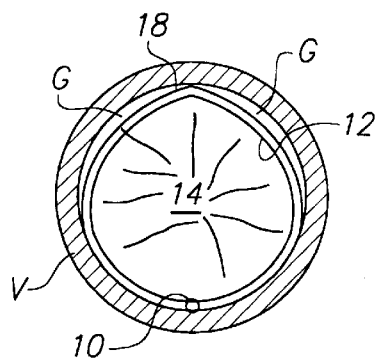
FIG. 1A (PRIOR ART)
FIG. 1B (PRIOR ART)
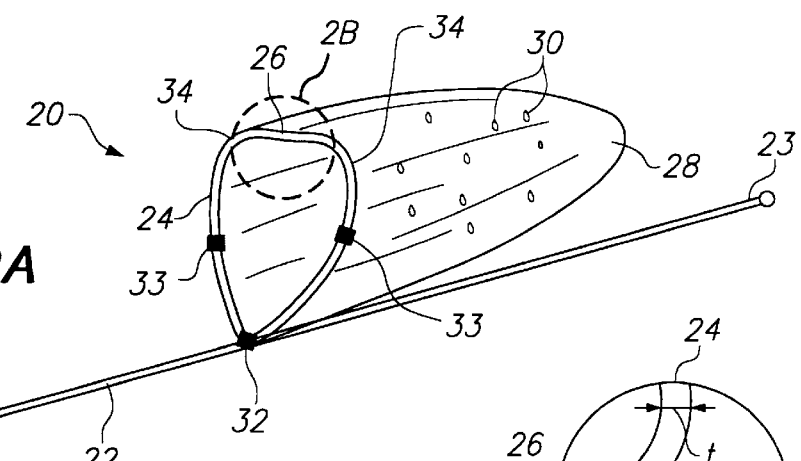
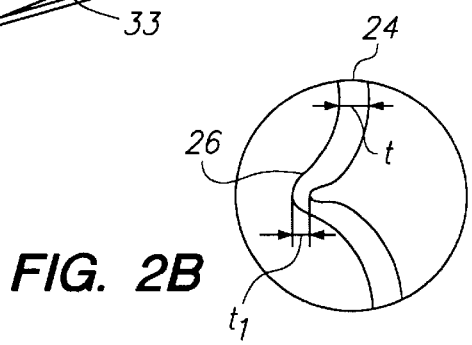
FIG. 2A
FIG. 2B
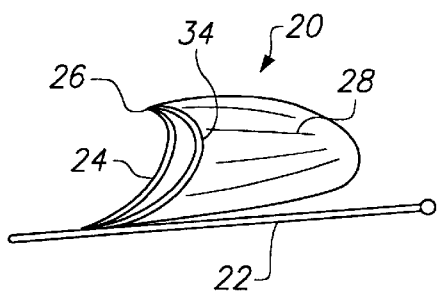
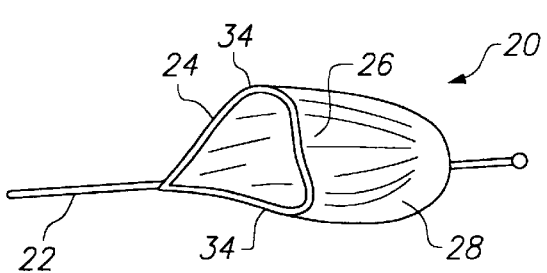
FIG. 3
FIG. 4

VASCULAR DEVICE HAVING ARTICULATION REGION AND METHODS OF USE

FIELD OF THE INVENTION

The present invention relates to apparatus and methods for filtering or removing matter from within a vascular system. More particularly, the present invention provides a low profile self-expanding vascular device useful capturing emboli generated during interventional procedures, and for thrombectomy and embolectomy.

BACKGROUND OF THE INVENTION

Percutaneous interventional procedures to treat occlusive vascular disease, such as angioplasty, atherectomy and stenting, often dislodge material the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, also involves the introduction of foreign objects into the bloodstream, and also may result in the formation of clots or release of emboli. Such particulate matter, if released into the bloodstream, also may cause infarction or stroke.

Numerous previously known methods and apparatus have been proposed to reduce the risk of embolism. Zadno-Azizi et al. U.S. Pat. No. 5,833,644, for example, describes the use of balloon-tipped catheter to temporarily occlude flow through a vessel from which a stenosis is to be removed. Stenotic material removed during a treatment procedure are evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as an angioplasty balloon or stent delivery system are advanced along the guide wire. The filter is designed to capture emboli generated during treatment of the stenosis while permitting blood to flow through the filter. Similar filter systems are described in Wholey et al. U.S. Pat. No. 4,723,549 and Cassell et al. U.S. Pat. No. 5,827,324.

One disadvantage of radially expandable filter systems such as described in the foregoing patents is the relative complexity of the devices, which typically comprise numerous parts. Connecting more than a minimal number of such parts to a guide wire generally reduces the ability of the guide wire to negotiate tortuous anatomy, and increases the profile of the device in its delivery configuration. Consequently, it may be difficult or impossible to use such devices in small diameter vessels such as are commonly found in the carotid artery and cerebral vasculature. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly, and is expected to result in a delivery profile too large to permit use of the device in critical regions of the body, such as the smaller coronary arteries, carotid arteries, and cerebral vasculature.

In view of the foregoing disadvantages of previously known apparatus and methods, it would be desirable to provide a vascular device, e.g., for use as a vascular filter that, overcomes such disadvantages, and employs few components.

It also would be desirable to provide a vascular device that is capable of being contracted to a small delivery profile, thus permitting use of the device in small vessels.

It further would be desirable to provide a vascular device that is capable of being contracted to a sufficiently small profile that it may be retrieved using the guide wire lumen of previously known treatment devices, and without the need for specialized delivery catheters.

It still further would be desirable to provide a vascular device that reduces the risk of emboli or thrombus removed from the vessel wall escaping from the device when the device is collapsed and removed.

SUMMARY OF THE INVENTION

In view of the foregoing, it is an object of the present invention to provide a vascular device that overcomes disadvantages of previously known vascular filters and thrombectomy/embolectomy devices, and employs few components.

It also is an object of this invention to provide a vascular device that is capable of being contracted to a small delivery profile, thus permitting use of the device in small vessels.

It is a further object of the present invention to provide a vascular device that is capable of being contracted to a sufficiently small profile that it may be retrieved using the guide wire lumen of previously known treatment devices, and without the need for specialized delivery catheters.

It is another object of this invention to provide a vascular device that reduces the risk of emboli or thrombus removed from the vessel wall escaping from the device when the device is collapsed and removed.

These and other objects of the present invention are accomplished by providing a vascular device, suitable for use as a vascular filter or thrombectomy/embolectomy device that comprises a blood permeable sac affixed at its perimeter to a support hoop having an articulation region. The support hoop is attached in a distal region of an elongated member, such as a guide wire, and supports a proximally-oriented mouth of the sac when the device is deployed in a vessel. In accordance with the principles of the present invention, the support hoop includes a reduced-thickness articulation region, generally opposite the point of attachment of the support hoop to the guide wire, that enables the support hoop to be contracted to very small radii of curvature without the problems of increased stiffness and kinking of previously known devices.

The support hoop preferably also has a curved profile, so that the articulation region is oriented in a direction approximately parallel to a vessel wall when the vascular device is deployed. This prevents the articulation region, when folded, from damaging the wall of the vessel, and permits the device to effectively contact the walls of the vessel and reduce emboli or thrombus removed from the vessel wall from bypassing the sac. Moreover, the articulation region when combined with a support hoop having a curved profile, causes the sides of the support hoop to fold inwards towards one-another when the vascular device is collapsed into a sheath for removal. This in turn closes the mouth of the sac and reduces the potential for emboli or thrombus to be released from the vascular device during removal.

Advantageously, use of an articulation region permits the vascular device of the present invention to be contracted to very small diameters, thereby enabling the use of delivery catheters having diameters as small as 3 Fr. Moreover, the vascular device of the present invention may be retracted within the guide wire lumen of conventional treatment devices, such as angioplasty catheters and stent delivery systems, thereby obviating the need to re-insert a specialized delivery catheter to remove the vascular device.

In embodiments of the system of the present invention suitable for use as embolic filters, the vascular device may include a separate guide wire for introducing treatment devices proximal to the deployed vascular device, and the support hoop may form one or more additional loops or turns when deployed in a vessel to enhance the stability of the filter within the vessel. In yet other embodiments, a delivery sheath is provided that permits a lesion to first be crossed with an unencumbered guide wire, prior to passing the vascular device across the lesion. Methods of using the vascular device of the present invention are also provided, including, in the context of a vascular filter, the use of a previously known balloon catheter to arrest antegrade flow through a vessel until the vascular device of the present invention is deployed.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 1A and 1B are, respectively, a side sectional side of a previously known vascular device contracted within a delivery sheath and an end view of that vascular device deployed in a vessel;

FIGS. 2A and 2B are, respectively, a perspective view of a vascular device constructed in accordance with the principles of the present invention in a deployed state, and a detailed view of the articulation region of the device of FIG. 2A;

FIG. 3 is a perspective view of the vascular device of the present invention in a folded configuration, prior to removal;

FIG. 4 is a plan view of the vascular device of FIG. 2A;

DETAILED DESCRIPTION OF THE INVENTION

Figure 5A:
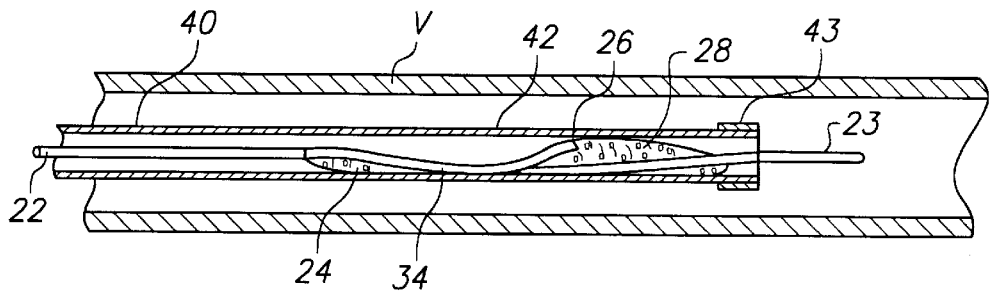
FIGS. 5A–5D are side sectional views depicting a method of deploying, using and retrieving the vascular device of the present invention.

Referring to FIGS. 1A and 1B, some of the disadvantages associated with previously known vascular devices, such as the emboli filters described in the above-mentioned International Publication WO 98/39053, are described. Vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of a vessel.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.035" or smaller are used, a hoop of nitinol or multi-strand nitinol cable having a diameter of 0.0055 inches will form kink 18. Kink 18 in turn may apply relatively high localized pressure and friction against wall 17 of sheath 16, thereby making the vascular filter difficult to deploy. In particular, the kink may impale wall 17 of delivery sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular device of the present invention solves the above-described disadvantages, providing a vascular device, suitable for use as a vascular filter or thrombectomy/embolectomy device, with a self-expanding support hoop that is sufficiently thick to radially expand and urge a blood permeable sac into engagement with the vessel wall, but which includes an articulation region that overcomes the problems associated with kinking. In particular, the vascular device of the present invention includes a reduced thickness articulation region and a pre-formed curved profile that avoids the difficulties of previously known systems while providing a high degree of efficacy in capturing emboli or thrombus, and ease of deployment and retrieval.

Referring now to FIGS. 2A and 2B, vascular device 20 constructed in accordance with the principles of the present invention, illustratively an embolic filter, comprises guide wire 22, support hoop 24 having articulation region 26, and blood permeable sac 28 affixed to support hoop 24. Sac 28 is coupled to support hoop 24 so that the support hoop 24 forms an opening for the sac. Support hoop 24 preferably is connected to guide wire 22 near distal end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof, and includes openings or pores 30 that permit blood cells to pass through the sac substantially unhindered, while capturing any larger emboli that may be released during a procedure such as angioplasty or stent placement. In a preferred embodiment, sac 28 has openings or pores 30 in a range of about 20 to 400 microns in diameter, and more preferably, about approximately 80 microns. These pores sizes will permit red blood cells (which have a diameter of approximately 5 microns) to easily pass through the sac. If sac 28 comprises a woven material, such as formed from the above-mentioned polymers, the pore size of the sac may be determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular device 20, described hereinafter, support hoop 24 folds in half and collapses to fit within a small diameter delivery sheath. When vascular device 20 is in a deployed state, as depicted in FIG. 2A, support hoop 24 resumes its pre-formed shape. Support hoop 24 preferably comprises nitinol wire, although it also be formed from a multistrand nitinol cable, or other super-elastic material.

In accordance with the principles of the present invention, support hoop 24 includes reduced-thickness articulation region 26 disposed opposite to point 32 at which support hoop 24 is affixed to guide wire 22. More specifically, support hoop 24 is pre-formed to form a structure having curved regions 34, so that articulation region 26 is disposed in a portion of the support hoop that is approximately parallel to a vessel wall when vascular device 20 is deployed. As depicted in FIG. 2B, articulation region 26 includes a region having reduced thickness $t_1$ compared to thickness t of the remainder of support hoop 24. Articulation region 26 and curved regions 34 enable support hoop 24 to fold with a pre-determined shape when vascular device 20 is collapsed to a contracted state for delivery or retrieval.

In FIG. 2B, articulation region 26 is depicted as a localized reduction in the thickness of support hoop 24, as may be achieved using conventional grinding or etching processes. Alternatively, support hoop 24 may be continuously tapered along its circumference, so that articulation region results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In a preferred embodiment of the vascular device 20 of the present invention, vascular device 20 easily fits within a delivery sheath having an inner diameter of 0.033", and more preferably, may be used with a delivery sheath having an inner diameter as small as 0.026". The deployed diameter of support hoop 24 preferably is approximately 7 mm, while guide wire 22 preferably has a diameter of 0.014", and tapers at its distal end. The distal end of guide wire 22 also may be tipped with a spring section, or coil tip (not shown).

Support hoop 24 preferably is constructed of 0.0055" nitinol wire tapered (by a grinding process) to 0.0025" at articulation region 26. Specifically, articulation region 26 preferably consists of a length about 0.05" long and having a diameter of 0.0025", coupled on either side to curved regions 34. Each of curved regions 34 includes of a length of wire that is tapered from a diameter of 0.055" to a diameter of 0.0025" over a length of about 0.025". Support hoop 24 also may include radiopaque features, such as gold or platinum bands 33 spaced at intervals around the circumference of support hoop 24.

With respect to FIGS. 3 and 4, additional features of vascular device 20 are described. FIG. 3 depicts vascular device 20 of FIG. 2A in a contracted state, while FIG. 4 provides a clearer view of the directional change in support hoop 24 caused by the presence of curved regions 34. In particular, FIG. 4 illustrates how curved regions 34 orient articulation region 26 in a direction parallel to the axis of guide wire 22.

Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac then would otherwise be possible, without increasing the risk of material escaping from the device when the sac is collapsed for retrieval. Use of a smaller or shallower sac also enables vascular device 20 to be delivered in a smaller delivery sheath, having an inner diameter as small as 0.026" for the preferred embodiment.

Referring now to FIGS. 5A–5D, methods of using the vascular device of the present invention as a vascular filter are described. In FIG. 5A, guide wire 22 is manipulated into position within vessel V using well-known percutaneous techniques. Vascular device 20 of FIG. 2A is disposed in its contracted delivery state within distal end 42 of delivery sheath 40 and delivery sheath 40 is advanced through the vessel using distal end 23 of guide wire 22. Articulation region 26 and curved regions 34 of support hoop 24 enable the sides of the support hoop to fold together and become elongated when drawn within delivery sheath 40.

Figure 5B:
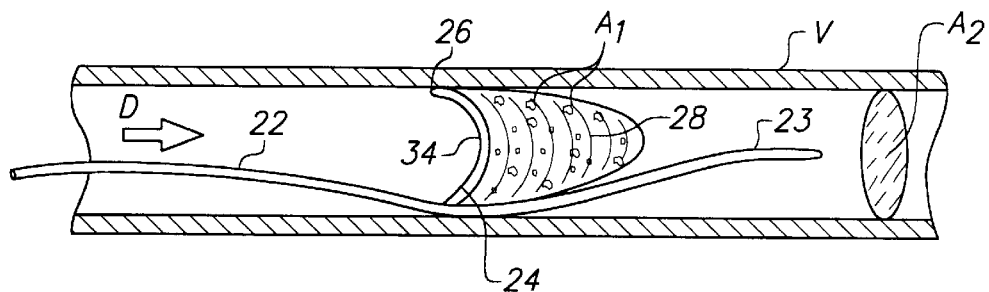

With respect to FIG. 5B, once delivery sheath 40 is disposed at a desired location within a patient's vessel V, such as a coronary artery or carotid artery, for example, based on the position of radiopaque band 43 under a fluoroscope, guide wire 22 is held stationary while delivery sheath 40 is retracted proximally. Alternatively, delivery sheath 40 may be held stationary while guide wire 22 is advanced. In either case, when vascular device 20 is no longer confined within delivery sheath 40, support hoop 24 expands to seal against the walls of the vessel V. When in its deployed state, curved regions 34 of support hoop 24 orient articulation region 26 so that it lies along the axis of the vessel, rather than impaling the vessel wall as is expected to be the case for the kinked support hoop of FIG. 1B. Blood continues to flow unimpeded through vessel V in direction A.

Figure 5C:
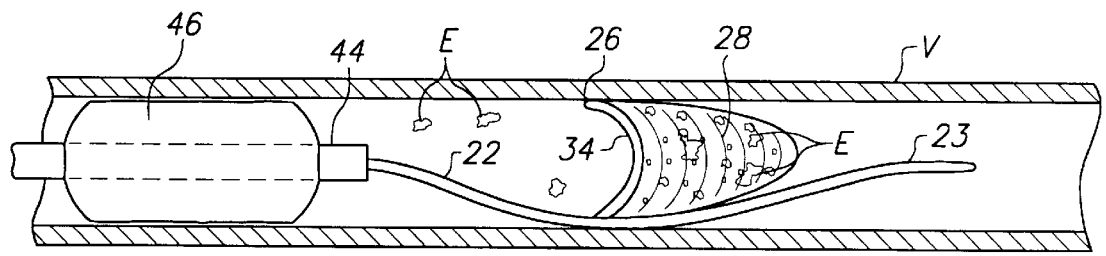

In FIG. 5C, once vascular device 20 is deployed in vessel V, other interventional instruments, such as angioplasty catheters, atherectomy devices, or stent delivery systems may be advanced along guide wire 22 to position such devices to treatment zones located proximally of vascular device 20. For example, in FIG. 5C, angioplasty balloon catheter 44 has been advanced along guide wire 22 to a position proximal of vascular device 20 to trap emboli E, i.e., pieces of plaque dislodged from the walls of vessel V by balloon 46.

Figure 5D:
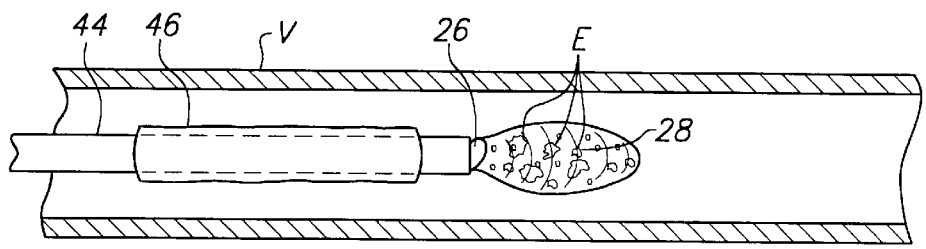

With respect to FIG. 5D, upon completion of the angioplasty procedure using angioplasty balloon catheter 44, guide wire 22 is pulled proximally to cause the sides of support hoop 24 to collapse together to close the mouth of sac 28 (see FIG. 3). Additional proximal retraction of guide wire 22 causes support hoop 24 and sac 28 to enter at least partially within the guide wire lumen of angioplasty catheter 44. As depicted in FIG. 5D, only a portion of support hoop 24, near articulation region 26, and a distal portion of sac 28 extend out of the guide wire lumen of angioplasty catheter 44. Angioplasty catheter 44 then is withdrawn with vascular device 20 and any trapped emboli E.

Advantageously, the compliant design of vascular device 20 permits the device to be contracted to its delivery state within the guide wire lumen of conventional previously known interventional devices. Accordingly, unlike previously known vascular devices, which require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

Alternatively, vascular device 20 may be used in performing thrombectomy/embolectomy. In this case, vascular device is deployed in a vessel at a location distal to a lesion, in the manner depicted in FIGS. 5A and 5B. Once support hoop 24 is deployed into contact with the vessel wall, guide wire 20 may be retracted proximally to scrape along the wall of the vessel, and excise thrombus so that it is captured in sac 28. Delivery sheath 44 may then be re-inserted into the vessel along guide wire 20 and vascular device 20 is retracted and removed from the vessel.

Figure 6:
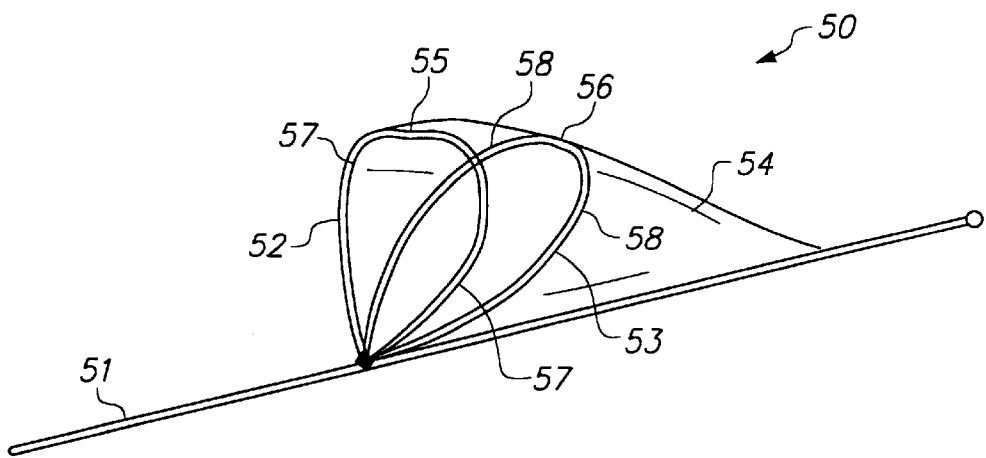
FIG. 6 is a perspective view of an alternative embodiment of the vascular device of the present invention in a deployed state.

Referring now to FIG. 6, an alternative embodiment of the vascular device of the present invention, again illustratively a vascular filter, is described. Vascular device 50 comprises guide wire 51 and support hoops 52 and 53 connected to blood permeable sac 54. As discussed hereinabove, vascular device 50 includes articulation regions 55 and 56 formed at the intersection of opposing curved regions 57 and 58 of support hoops 52 and 53. Sac 54 preferably also is connected to guide wire 51 along its entire length, thereby providing more controlled deployment and removal of vascular device 50. Support hoop 54 serves to stabilize and deploy the distal portion of sac 54. In addition, affixing sac 54 to guide wire 51 may provide a more compact arrangement within a delivery sheath, and prevent bunching of the sac material. Vascular device 50 preferably is deployed using a separate second guide wire (not shown) over which interventional devices may be advanced.

Figure 7A:
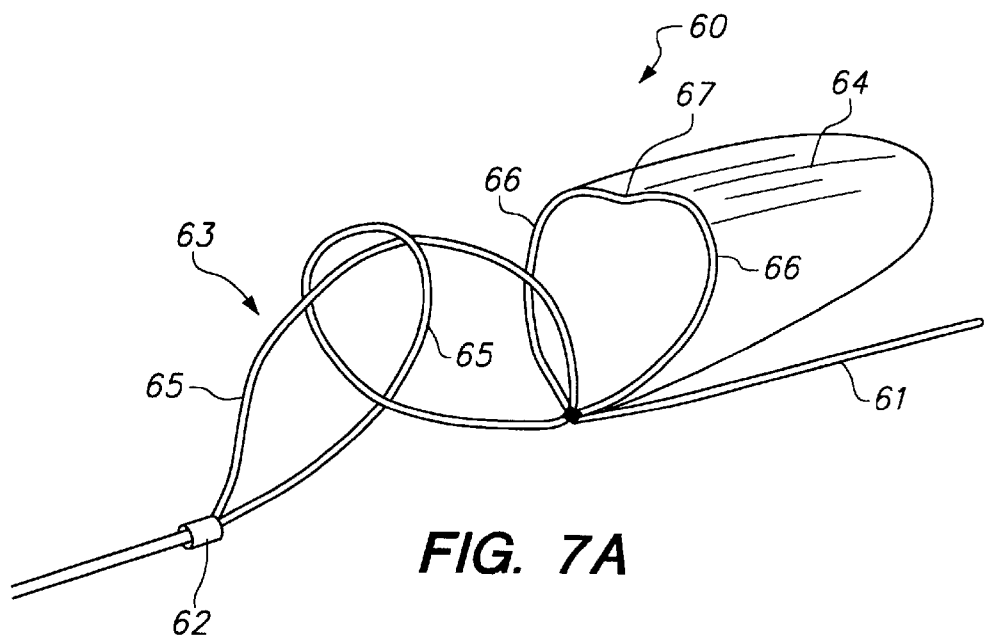
FIGS. 7A and 7B are, respectively, a perspective view and a plan view of a further alternative embodiment of a vascular device of the present invention in a deployed state.
Figure 7B:
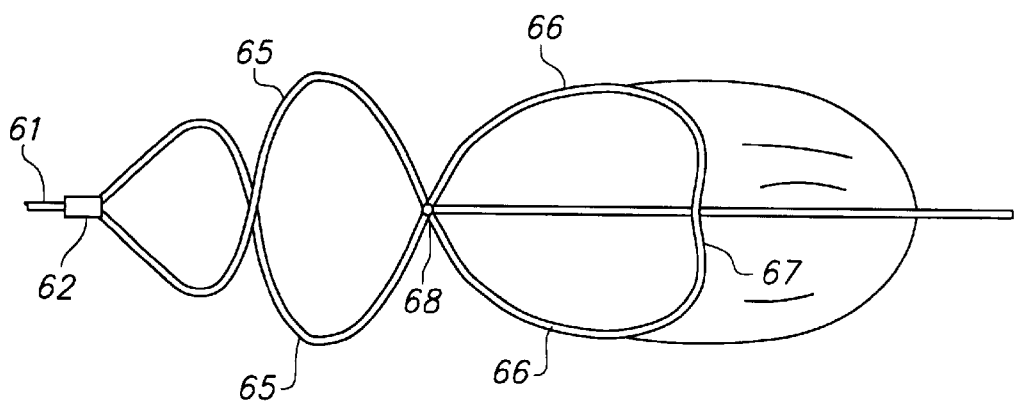

In FIGS. 7A and 7B, a further alternative embodiment of the vascular device of the present invention is described. Vascular device 60, shown in the deployed state, comprises guide wire 61 having multi-turn helical support hoop 63 connected at weld point 62. Blood permeable sac 64 is affixed to the distal-most portion of support hoop 63. Support hoop 63 includes one or more side turns 65 that terminate in curved regions 66, as described hereinabove. Curved regions 66 in turn are joined together by articulation region 67. Preferably, side turns 65 are coupled to one another and to the distal region of guide wire 61, e.g., by a weld bead, at point 68.

In accordance with this aspect of the present invention, vascular device 60 may be contracted to small profile delivery state. When deployed from a delivery catheter, such as delivery sheath 40 of FIG. 5A, side turns 65 expand into contact with the walls of the vessel proximal to the location at which curved regions 66 contact the vessel wall. Side turns 65 serve to stabilize the support hoop 63 and sac 64 when vascular device 60 is deployed within a blood vessel. In addition, side turns 64 are expected to assist in orienting the axis of support hoop 63 and sac 64 in alignment with the longitudinal axis of vessel V. Accordingly, support hoop 63 is expected to reduce the risk of tilting of the vascular device within the vessel, and thus enhance the safety and reliability of the device.

Figure 8A:
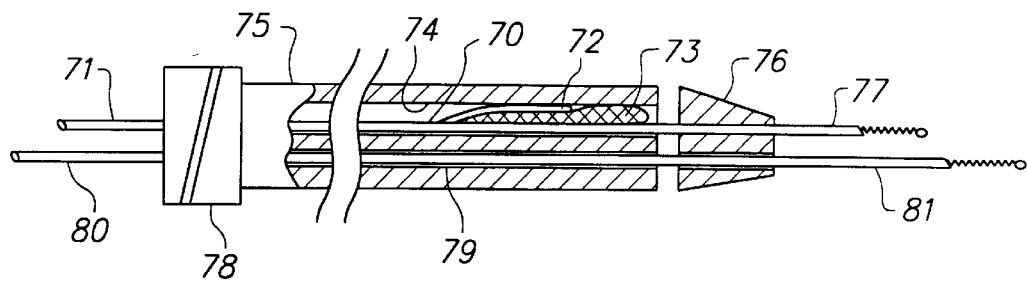
FIGS. 8A to 8C are sectional views of an alternative embodiment of the vascular device of the present invention disposed within a delivery sheath.
Figure 8B:
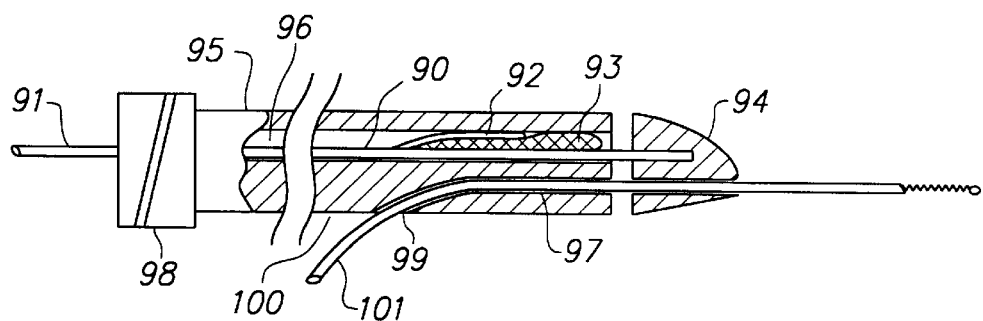
Figure 8C:
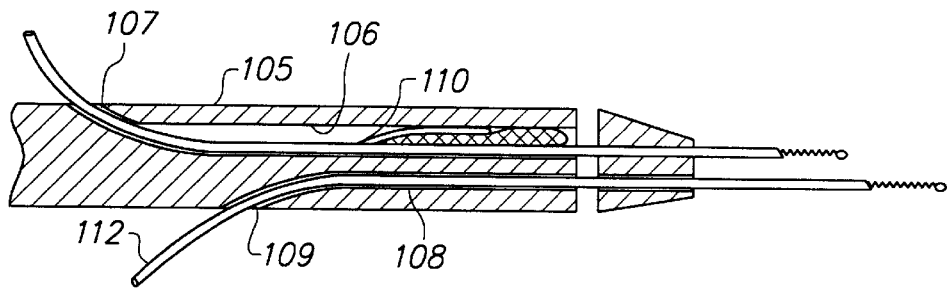

Referring now to FIGS. 8A to 8C, several embodiments of a delivery sheath suitable for use with the vascular device of the present invention are described. Each of these embodiments are designed to permit the physician to first pass an unencumbered guide wire across a lesion before passing the vascular device of the present invention across the lesion. Thus, the risk of generating emboli, during the step of positioning the vascular device of the present invention distal to a lesion, is expected to be reduced.

In particular, in FIG. 8A, vascular device 70 of the present invention comprises guide wire 71, support hoop 72 and blood permeable sac 73 folded in a contracted delivery state within lumen 74 of delivery sheath 75. Vascular device 70 is similar in design to vascular device 20 of FIG. 2A, except that device 70 includes nose cone 76 affixed to distal region 77 of guide wire 71. Delivery sheath 75 includes hemostatic fitting 78 at its proximal end and guide wire lumen 79.

In accordance with the methods of the present invention, vascular device 70 and guide wire 80 are used as follows. First, unencumbered guide wire 80 is advanced through a vessel until distal region 81 of the guide wire crosses the lesion. The proximal end of guide wire 80 then is inserted into the distal end of guide wire lumen 79 of delivery sheath 75 using previously known "over the wire" techniques.

Delivery sheath 75 then is advanced over guide wire 80, which is held stationary, until nose cone 76 and a distal portion of the delivery sheath cross the lesion. Once support hoop 72 and sac 73 of vascular device 70 are positioned distal to the lesion, delivery sheath 75 is retracted proximally, thereby deploying vascular device 70 to its deployed state. As will of course be understood, nose cone 76 remains in the vessel, distal to sac 73, during deployment of the vascular device. Upon completion of use of vascular device 70, delivery sheath 75 may once again be advanced along guide wire 71 and the support hoop and sac retracted within lumen 74 of delivery sheath 75.

Vascular device 90 of FIG. 8B is similar in construction to that of FIG. 8A, and includes guide wire 91, support hoop 92, blood permeable sac 93 and nose cone 94. Delivery sheath 95 includes lumen 96 housing device 90 and guide wire lumen 97 and hemostatic fitting 98. Guide wire lumen 97 opens through skive 99 in the lateral wall 100 of delivery sheath 95. Guide wire 101 therefore may be used in accordance with well-known "rapid exchange" techniques, wherein the length of unencumbered guide wire 101 may be significantly shorter than in the case of the "over the wire" arrangement depicted in FIG. 8B. Operation of delivery sheath 95 and vascular device 90 is similar to that described hereinabove with respect to FIG. 8A, except that the proximal end of unencumbered guide wire 101 is passed through the distal end of lumen 97 and passes out through skive 99.

In FIG. 8C, delivery sheath 105 includes lumen 106 that opens through the lateral wall via skive 107, and guide wire lumen 108 that opens through the lateral wall via skive 109. Accordingly, as will be apparent to one of ordinary skill, both vascular device 110 and guide wire 112 may be used as described hereinabove with respect to FIG. 8A and further in accordance with "rapid exchange" techniques.

Figure 9:
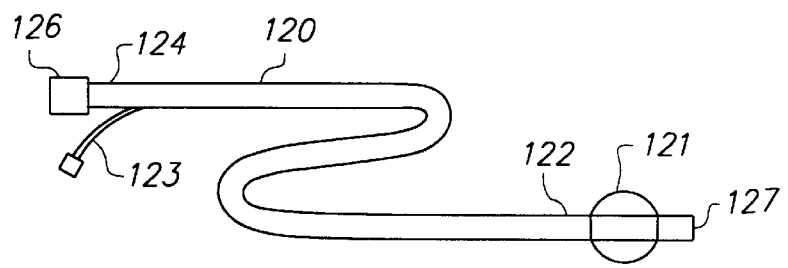
FIG. 9 is a side view of a previously known balloon catheter.

Referring now to FIG. 9, a previously known balloon catheter is described. Catheter 120 is constructed of materials typically used in catheters, such as polyethylene or polyurethane, and includes compliant balloon 121 disposed in distal region 122. Compliant balloon, which may be formed of nylon or latex, is inflated using inflation port 123 at proximal end 124 of the catheter. Catheter 125 also includes hemostatic port 126 and an interior lumen through which a delivery sheath may be advanced to pass out of an opening in distal end 127.

Figure 10A:
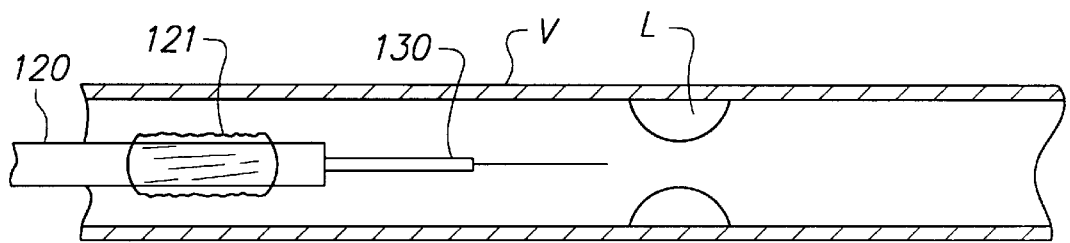
FIGS. 10A to 10D are views illustrating the steps of using the balloon catheter of FIG. 9 with the vascular device of FIG. 2.
Figure 10B:
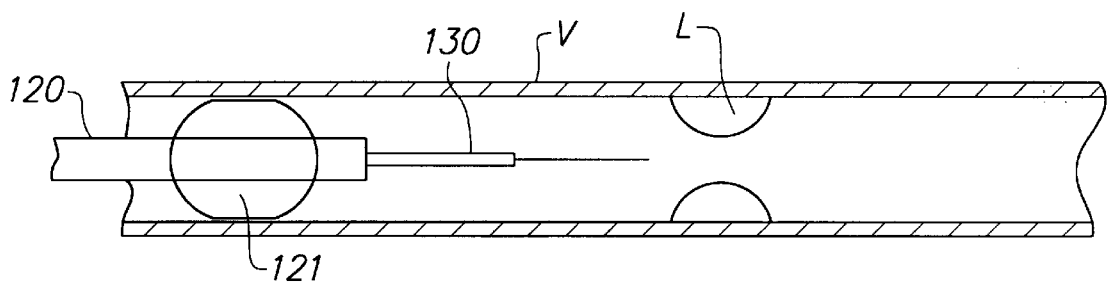
Figure 10C:
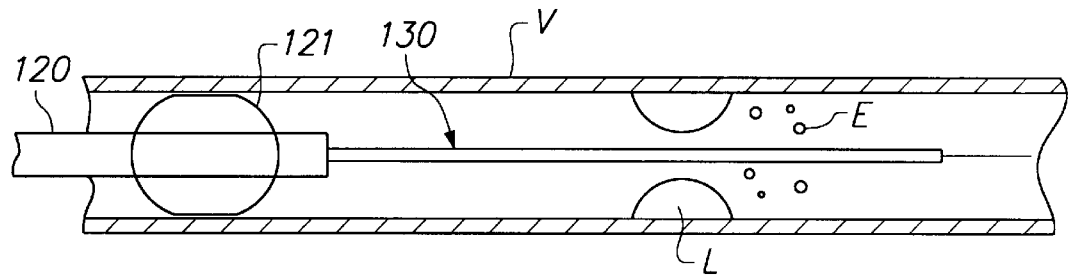

With respect to FIGS. 10A to 10C, a method of using catheter 120 of FIG. 9 in conjunction with the vascular device of the present invention is described. In accordance with this aspect of the present invention, antegrade blood flow through a vessel is occluded while a vascular device constructed in accordance with the present invention is advanced across a lesion. Once the vascular device, illustratively a vascular filter, is deployed, the balloon is deflated, thereby permitting antegrade flow to be established. Importantly, because flow through the vessel is stopped prior to deployment of the vascular device, few or no emboli are expected to bypass the filter.

More particularly, with respect to FIG. 10A, catheter 120 is disposed in vessel V at a location proximal to lesion L, with the vascular device of the present invention disposed in its contracted delivery state in delivery sheath 130. In FIG. 10B, balloon 121 is inflated via inflation port 123 to engage the interior wall of vessel V, thereby arresting antegrade flow in the vessel.

As shown in FIG. 10C, delivery sheath 130 then is advanced across lesion L so that the support hoop and sac of the vascular device will be disposed distal to lesion L when deployed. During this step, delivery sheath 130 may generate emboli E as it passes across the lesion. However, because antegrade flow in the vessel is stopped, the emboli will not travel distally in the vessel.

Figure 10D:
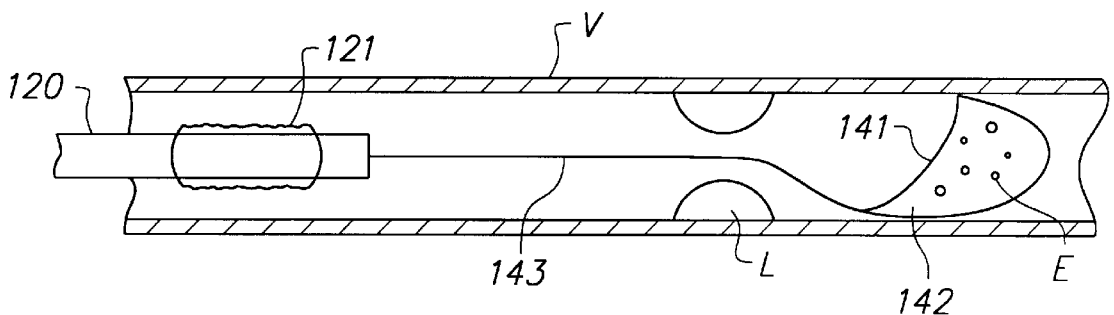

With respect to FIG. 10D, once vascular device 140 is deployed, so that support hoop 141 and sac 142 span vessel V, balloon 121 is deflated. This in turn causes antegrade flow to become re-established in vessel V, urging emboli E into sac 142. Catheter 120 then may be withdrawn, and additional treatment devices advanced along guide wire 143 of vascular device 140. Removal of vascular device 140 may be by any of the methods described hereinabove with respect to FIG. 5D.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus suitable for filter emboli or performing thrombectomy or embolectomy comprising:
   an elongated member having a distal region;
   a support structure attached to the distal region, the support structure having an articulation region interposed between curved regions that orient the articulation region relative to a vessel wall when the support structure is deployed within a vessel; and
   a blood permeable sac affixed to the support structure so that the support structure forms a mouth of the blood permeable sac,
   wherein the opposite sides of the support structure close towards one another when the apparatus is contracted to a contracted configuration.

2. The apparatus of claim 1, wherein the blood permeable sac comprises a biocompatible material.

3. The apparatus of claim 2, wherein the biocompatible material comprises a material chosen from a list consisting of polyethylene, polypropylene, polyester, polyurethane and nylon.

4. The apparatus of claim 1, wherein the blood permeable sac comprises a woven material having a plurality of pores, the pores having a size determined by a weave pattern of the woven material.

5. The apparatus of claim 4, wherein each one of the plurality of pores has a diameter in a range of 20 to 400 microns.

6. The apparatus of claim 1, wherein the support structure comprises a super-elastic material.

7. The apparatus of claim 6, wherein the super-elastic material comprises a nickel-titanium alloy.

8. The apparatus of claim 1, wherein the support structure comprises a wire having a thickness that tapers to a minimum thickness at the articulation region.

9. The apparatus of claim 1, wherein the apparatus has a deployed state, wherein the support structure engages an interior wall of a patient's vessel, and a delivery state, wherein the apparatus has the contracted configuration to permit insertion within a delivery sheath.

10. The apparatus of claim 9, wherein the support structure is folded at the articulation region when the apparatus is in the delivery state.

11. The apparatus of claim 9, wherein the mouth of the blood permeable sac is closed when the apparatus is in the contracted configuration, thereby preventing emboli from escaping from the blood permeable sac.

12. The apparatus of claim 1, wherein the support structure comprises a radiopaque band.

13. The apparatus of claim 1, wherein the blood permeable sac is affixed to the elongated member along a length of the blood permeable sac.

14. The apparatus of claim 1 wherein the support structure includes one or more side turns that stabilize and orient the apparatus in the deployed state.

15. The apparatus of claim 1 wherein the elongated member serves as a guide wire.

16. The apparatus of claim 1 further comprising:
   a nose cone disposed on the distal region of the elongated member distal to the support structure; and
   a delivery sheath having a first lumen for accepting the elongated member, support structure and blood permeable sac, and a second lumen for accepting a guide wire.

17. The apparatus of claim 16 wherein the first lumen of the delivery sheath opens to a skive in a lateral wall of the delivery sheath in a distal region of the delivery sheath.

18. The apparatus of claim 16 wherein the second lumen of the delivery sheath opens to a skive in a lateral wall of the delivery sheath in a distal region of the delivery sheath.

19. The apparatus of claim 1 further comprising a balloon catheter.

20. A method of trapping emboli or thrombus during a medical procedure, the method comprising:

providing apparatus comprising an elongated member, a support structure having an articulation region coupled to the elongated member, and a blood permeable sac affixed to the support structure so that the support structure forms a mouth of the blood permeable sac;

positioning the apparatus in a contracted delivery state within a delivery sheath;

advancing the delivery sheath to a desired location within a patient's vessel;

withdrawing the delivery sheath to expand the apparatus to a deployed state wherein the support structure seals against the vessel wall;

providing an interventional device for performing a medical procedure, the interventional device comprising a guide wire lumen;

percutaneously and transluminally advancing the interventional device along the elongated member to position the interventional device within the patient's vessel at a location proximal of the apparatus; and performing the medical procedure, the apparatus catching emboli released when the medical procedure is performed.

21. The method of claim 20 further comprising:

retracting the apparatus into a collapsed configuration within the guide lumen of the interventional device; and removing the interventional device and apparatus from the patient's vessel.

22. The method of claim 21, wherein retracting the apparatus within the guide wire lumen comprises folding the support structure at the articulation region to close the mouth of the blood permeable sac.

23. The method of claim 20, further comprising, prior to advancing the delivery sheath to a desired location within a patient's vessel:

providing a catheter having a balloon in a distal region;

inserting the catheter so that the balloon is disposed proximally of a lesion; and inflating the balloon to arrest antegrade flow through the vessel, wherein advancing the delivery sheath to a desired location within a patient's vessel comprises advancing the delivery sheath through an interior lumen of the catheter so that a distal region of the delivery sheath is disposed distal to the lesion.

24. The method of claim 23, further comprising, after withdrawing the delivery sheath to expand the apparatus, deflating the balloon to re-establish antegrade flow through the vessel.

25. The method of claim 20 further comprising:

partially retracting the apparatus into a collapsed configuration within the guide lumen of the interventional device; and removing the interventional device and apparatus from the patient's vessel.

26. Apparatus suitable for filtering emboli or performing thrombectomy or embolectomy comprising:

an elongated member having a distal region;

a support structure comprising a super-elastic material attached to the distal region, the support structure having an articulation region interposed between curved regions that orient the articulation region relative to a vessel wall when the support structure is deployed within a vessel; and a blood permeable sac affixed to the support structure so that the support structure forms a mouth of the blood permeable sac.

27. The apparatus of claim 26, wherein the blood permeable sac comprises a biocompatible material.

28. The apparatus of claim 27, wherein the biocompatible material comprises a material chosen from a list consisting of polyethylene, polypropylene, polyester, polyurethane and nylon.

29. The apparatus of claim 26, wherein the blood permeable sac comprises a woven material having a plurality of pores, the pores having a size determined by a weave pattern of the woven material.

30. The apparatus of claim 29, wherein each one of the plurality of pores has a diameter in a range of 20 to 400 microns.

31. The apparatus of claim 26, wherein the super-elastic material comprises a nickel-titanium alloy.

32. The apparatus of claim 26, wherein the support structure comprises a wire having a thickness that tapers to a minimum thickness at the articulation region.

33. The apparatus of claim 26, wherein the apparatus has a deployed state, wherein the support structure engages an interior wall of a patient's vessel, and a delivery state, wherein the apparatus has a contracted configuration to permit insertion within a delivery sheath.

34. The apparatus of claim 33, wherein the support structure is folded at the articulation region when the apparatus is in the delivery state.

35. The apparatus of claim 33, wherein the mouth of the blood permeable sac is closed when the apparatus is in the contracted configuration, thereby preventing emboli from escaping from the blood permeable sac.

36. The apparatus of claim 26, wherein the support structure further comprises a radiopaque band.

37. The apparatus of claim 27, wherein the blood permeable sac is affixed to the elongated member along a length of the blood permeable sac.

38. The apparatus of claim 26 wherein the support structure includes one or more side turns that stabilize and orient the apparatus in the deployed state.

39. The apparatus of claim 26 wherein the elongated member serves as a guide wire.

40. The apparatus of claim 26 further comprising:

a nose cone disposed on the distal region of the elongated member distal to the support structure; and a delivery sheath having a first lumen for accepting the elongated member, support structure and blood permeable sac, and a second lumen for accepting a guide wire.

41. The apparatus of claim 40 wherein the first lumen of the delivery sheath opens to a skive in a lateral wall of the delivery sheath in a distal region of the delivery sheath.

42. The apparatus of claim 40 wherein the second lumen of the delivery sheath opens to a skive in a lateral wall of the delivery sheath in a distal region of the delivery sheath.

43. The apparatus of claim 26 further comprising a balloon catheter.

* * * * *